(12) United States Patent
Paul

(10) Patent No.: US 12,239,520 B2
(45) Date of Patent: *Mar. 4, 2025

(54) REINFORCEMENT DEVICE WITH DISSOLVABLE LAYER AND ITS USE

(71) Applicant: Covidien LP, Mansfield, MA (US)

(72) Inventor: Martin G. Paul, Rockville, MD (US)

(73) Assignee: Covidien LP, Mansfield, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 18/094,529

(22) Filed: Jan. 9, 2023

(65) Prior Publication Data

US 2023/0147002 A1  May 11, 2023

Related U.S. Application Data

(60) Continuation of application No. 16/581,620, filed on Sep. 24, 2019, now Pat. No. 11,547,543, which is a continuation of application No. 15/475,193, filed on Mar. 31, 2017, now Pat. No. 10,456,231, which is a continuation of application No. 15/339,010, filed on Oct. 31, 2016, now Pat. No. 9,629,703, which is a continuation of application No. 14/881,326, filed on Oct. 13, 2015, now Pat. No. 9,480,547, which is a continuation of application No. 14/620,749, filed on Feb. 12, 2015, now Pat. No. 9,186,236, which is a (Continued)

(51) Int. Cl.
*A61F 2/00* (2006.01)

(52) U.S. Cl.
CPC .... *A61F 2/0063* (2013.01); *A61F 2002/0068* (2013.01); *A61F 2210/0004* (2013.01); *A61F 2210/0076* (2013.01)

(58) Field of Classification Search
CPC ............ A61F 2/0063; A61F 2210/0004; A61F 2002/30062; A61F 2013/00655; A61F 2013/00676; A61F 2013/00757; A61L 27/3604; A61L 27/3687
See application file for complete search history.

(56) References Cited

U.S. PATENT DOCUMENTS 3,122,479 A   2/1964   Smith
4,563,184 A   1/1986   Korol
(Continued)

OTHER PUBLICATIONS

Chastan, P. "Tension free open inguinal hernia repair using an innovative self gripping semi-resorbable mesh". J Min Access Surg 2006; 2: pp. 139-143.

(Continued)

*Primary Examiner* — Ashley L Fishback
(74) *Attorney, Agent, or Firm* — Weber Rosselli & Cannon LLP

(57) ABSTRACT

A reinforcement device for reinforcing tissues having one or more structural deficiencies includes a longitudinally-extending reinforcing layer for treating the structural deficiency, a plurality of spiked naps distributed across the reinforcing layer and projecting therefrom for adhering to the tissue, and a dissolvable matrix layer covering at least a portion of the reinforcing layer and a portion of the plurality of spiked naps. The matrix layer increases the time before the spiked naps substantially adhere to the tissue, thereby allowing the practitioner additional time to position the reinforcement device.

20 Claims, 4 Drawing Sheets

Related U.S. Application Data continuation of application No. 13/859,406, filed on Apr. 9, 2013, now Pat. No. 8,968,418, which is a division of application No. 12/783,936, filed on May 20, 2010, now Pat. No. 8,435,307.

(56) References Cited

U.S. PATENT DOCUMENTS

| | | | |
|---|---|---|---|
| 4,728,642 | A | 3/1988 | Pawelchak et al. |
| 6,191,334 | B1 | 2/2001 | Patterson |
| 6,596,002 | B2 | 7/2003 | Therin et al. |
| 6,627,215 | B1 | 9/2003 | Dale et al. |
| 8,435,307 | B2 | 5/2013 | Paul |
| 8,778,012 | B2 * | 7/2014 | Matheny ................ A61L 27/54 623/1.36 |
| 8,968,418 | B2 | 3/2015 | Paul |
| 9,186,236 | B2 | 11/2015 | Paul |
| 9,480,547 | B2 | 11/2016 | Paul |
| 9,629,703 | B2 | 4/2017 | Paul |
| 10,456,231 | B2 | 10/2019 | Paul |
| 11,547,543 | B2 | 1/2023 | Paul |
| 2012/0165937 | A1 | 6/2012 | Montanari et al. |
| 2012/0179175 | A1 | 7/2012 | Hammell |
| 2012/0197415 | A1 * | 8/2012 | Montanari ............. A61L 27/56 623/23.74 |

OTHER PUBLICATIONS

Dixit, R.P. et al. "Oral strip technology: Overview and future potential". Journal of Controlled Release 139 (2009), pp. 94-107.
"Parietex ProGrip Self-fixating Mesh", Hernia Repair Products. <http://www.covidien.com/campaigns/pagebuilder.aspx?topicID= 172431&pag- e=Hernia:Parietex> pp. 1-2.
"Procedures/Parietex ProGrip Self-Fixating Mesh", Hernia Solutions. <http://www.covidien.com/hernia/us/pages.aspx?page= Procedures/AWR/1864- 57/170538> (select United States) pp. 1-2.

* cited by examiner

REINFORCEMENT DEVICE WITH DISSOLVABLE LAYER AND ITS USE

CROSS-REFERENCE TO RELATED APPLICATIONS

This application is a continuation of U.S. patent application Ser. No. 16/581,620 filed Sep. 24, 2019, now U.S. Pat. No. 11,547,543, which is a continuation of U.S. Patent Application Ser. No. 15/475,193 filed Mar. 31, 2017, now U.S. Pat. No. 10,456,231, which is a continuation of U.S. patent application Ser. No. 15/339,010 filed Oct. 31, 2016, now U.S. Pat. No. 9,629,703, which is a continuation of U.S. patent application Ser. No. 14/881,326 filed Oct. 13, 2015, now U.S. Pat. No. 9,480,547, which is a is a continuation of U.S. patent application Ser. No. 14/620,749 filed Feb. 12, 2015, now U.S. Pat. No. 9,186,236, which is a continuation of U.S. patent application Ser. No. 13/859,406 filed Apr. 9, 2013, now U.S. Pat. No. 8,968,418, which is a divisional of U.S. patent application Ser. No. 12/783,936 filed May 20, 2010, now U.S. Pat. No. 8,435,307, and the disclosures of each of the above-identified applications are hereby incorporated by reference in their entirety.

BACKGROUND OF THE INVENTION

Field of Invention

The present invention relates generally to abdominal wall reinforcement devices, and in particular devices used for the treatment of inguinal hernias by either an anterior or laparoscopic route.

Description of the Related Art

Providing a permanent mechanical support for the repair of abdominal wall hernias is well known in the art. Various implants and surgical techniques have been developed to assist surgeons during reconstructive procedures to improve the outcome of such procedures, both in terms of its effectiveness and tolerance by the patient. It is known, for example, that reinforcement of the operative area by a mechanical implant is improved when the implant quickly integrates in the tissue. As disclosed in U.S. Pat. No. 6,596,002 (assigned to Sofradim), to achieve intimate and early integration of the implant without formation of a peripheral fibrous shell, the macroporosities of the implant must be as widely open as possible to the outside and the elasticity of the reinforcement must allow it to follow the physiological deformations of the wall onto which the device is placed. The suitability of such a device is related to the mechanical resistance of the textile material used to form the implant. It is reported that such resistance must be greater than 10 decanewtons using the standardized ISO5081 test. Such devices should prevent hernia recurrence through the pores of the tissue, which must be a maximum of 7 to 10 millimeters in diameter.

The invention disclosed in U.S. Pat. No. 6,596,002, involves a knitted mesh useful for the treatment of inguinal hernias by the anterior access route, which is placed in a premuscular location. The knitted mesh is characterized as affording the practitioner with an implant device that is easy to use, quickly securable in place, and that effectively repairs abdominal wall deficiencies. The knitted mesh includes a reinforcement piece and a flap piece connected to the reinforcement piece. The reinforcement piece is cut from an open-worked prosthetic knit web. The web is made of multifilament yarns. The reinforcement piece includes a radial slit and annular cut-out region approximately in the center of the reinforcement piece that allows the surgeon to place the piece around the spermatic cord. According to the patent, the reinforcement piece has the general shape of an ellipse, and it satisfies the requirements mentioned above. In particular, the shape allows the surgeon to cover all the potential parietal weakness. The device is described as being easy to put into place.

The aforementioned flap piece is made such that it may be folded over the slit on the reinforcement piece to close it. The flap is described as having a "gripping means" integral with the flap itself, or attached to it, for fastening or joining the flap piece to the knitted structure of the reinforcement piece. In one embodiment, the flap is described as having spike naps projecting from its face. The spiked naps are formed by a monofilament yarn and have a length allowing them to penetrate into and attach themselves to the knitted structure of the reinforcement piece without protruding from the latter. That is, on one end, the spiked naps are embedded into the knit web to secure them, and on the other end project above the surface of the flap piece, generally extending above the plane of the flap piece in a perpendicular direction. Depending on the particular applications for the device, the spike naps are made of a biocompatible polymer or of bioabsorbable material, such as polylactic acid (PLA). In use, the flap is folded over the reinforcement piece such that the spiked naps engage in and between the multifilament yarns of the knit of the reinforcement piece, similar to a hook and loop fastener. This ensures that the flap piece is locked in position, securely closing the slit and holding the spermatic cord in position. The spiked naps are not permanent, however. The flap piece may be unfastened and repositioned, if necessary.

The density of the spiked naps is reportedly determined as a function of the prosthetic knit being used, but is reportedly best in the range of between 50 and 90 naps per cm·sup·2. The length of the naps, measured from the base projecting from the attachment sheet to the top of the spike, will depend on the thickness of the prosthetic knit forming the reinforcement piece, but is reportedly best in the range between 1 and 2 millimeters.

In the aforementioned patent, the reinforcement piece is described as having a grip or gripping means, which is integral with the knit or attached to it, and is used for fastening or joining The same spiked naps described above may be used on one face of the reinforcement piece, just as they are used on the flap piece. The grip/gripping means devices project from one and/or the other of the faces of the knit, and are used to fasten or join the reinforcement piece to the tissues the device is place in contact with. The knit from which the reinforcement piece is made is described as a "flat knit" type or one having two porous layers connected by connecting yarns. The weave of the knit forms run-proof transverse channels opening out from the two porous layers.

A commercial embodiment of the knitted mesh device called ProGrip.™. is available from Covidien (Massachusetts). Its use is described in Philippe Chastan, M. D., "Tension-Free Open Inguinal Hernia Repair Using an Innovative Self Gripping Semi-Resorbable Mesh," published in the Journal of Minimal Access Surgery, 2006 (see pp 139-43 describing results based on a published study of the Parietene.™. (polypropylene) version of the ProGrip.™). In its literature, Covidien states that the biocompatible monofilament knit making up the knitted mesh is made from nonresorbable polyethylene teraphthalate (PET), and the spike naps are made from a resorbable poly lactic acid (PLA). The monofilament knit is hydrophilic, so it works with the body's natural systems to improve tissue integration while reducing foreign material response. The entire mesh with the spike naps reportedly provides "immediate fixation" to the underlying tissue. The knit material is substantially stronger than using fibrin glue, and is equivalent to incorporation by hernia stapler fixation at five days after placement. Compared to suture fixation, the device is 100% stronger at four weeks. The literature also notes that the device can be positioned and placed in less than 60 seconds, and unlike standard open repair of parietal deficiencies, the device does not require additional fixation methods. The device has a reported density of 73.0 g/m·sup·2 before resorption of the spiked naps, and a reported density of 38.0 g/m·sup·2 after resorption (a change of 53 g/m·sup·2 or 48-percent).

Despite the features and advantages of the invention described above, experience has shown that the spike naps may adhere too quickly for some applications, i.e., "immediate fixation" or adherence in less than 60 seconds. Removing the device (so it can be repositioned) is difficult after attachment, and it can be traumatic to the underlying tissue. Often, repositioning cannot be done, so a new device is requires, at relatively substantial expense to the patient or practitioner. Also, the device is expected to attach quickly to intra-abdominal tissues (e.g., smooth tissues such as bowel), and so the device is not useful for intra-abdominal implantation using, for example, laparoscopy instruments to place the device interiorly of, for example, an abdominal wall hernia. Accordingly, there exists a need for such a device.

It is well known in the medical arts to apply a measured amount of a spreadable "gel" to form a temporary layer, which may then provide the benefit of protecting, at least temporarily, another layer, material, or object, or to reduce the friction between two surfaces separated by the gel layer. Such a gel, if applied to the spiked naps of the aforementioned product, would reduce the gripping ability of the spiked naps and allow the practitioner to place and then replace the knitted mesh device before the spiked naps begin to adhere to the parietal tissues. However, if the gel has a high viscosity, the ability of the spiked naps to be reabsorbed by the underlying tissue may be greatly reduced, causing the knitted mesh to be too loose and require additional sutures. Also, low viscous gels are unsuitable from a manufacturing perspective, because they are difficult to apply to a mesh, and would require special or different packaging materials compared to a knitted mesh without a gel layer. Further, many gels may be easily disturbed by the practitioner's fingers and/or instruments used by the practitioner, thereby reducing or eliminating their effectiveness.

It is also well known in the medical arts to use adhesives to attach a device to a patient or substrate. An adhesive layer applies to the knitted mesh and/or spiked naps of the aforementioned device would immediately cause fixation, making it more difficult to remove or reposition. Also, unlike the spiked naps of the aforementioned knitted mesh device, an adhesive is generally not reabsorbed (at least not immediately), and so it can form (at least temporarily) a generally impenetrable layer between the device and the underlying tissue, which may not be desirable in certain applications.

It is also known in the medical arts to use a removable, protective film or layer over another layer. Thus, a film could be used over an adhesive layer on a device that prevents the adhesive from sticking until the device is used. Such protective films are relatively inexpensive to make from various inert, compatible, and stable polymeric materials. In use, the practitioner simply removes and discards the film, then positions the device and permanently places it using the underlying adhesive to hold the device in place. Adding a film to an adhesive layer may be feasible, but it may not be suitable for adding directly to the knitted mesh device described above without at least some adhesive between the file and underlying PET knit and PLA spiked naps extending from the knit. If the film attaches to the spiked naps, it may not be cleanly removable without destroying some of the spiked naps, thereby reducing the effectiveness of those devices for their intended purpose. Also, removing the film intra-abdominally presents all sorts of challenges to the practitioner and is, practically speaking, not feasible (i.e., the film would have to be removed exteriorly of the patient).

Accordingly, there exists a need for a material that reduces the time before the spiked naps of the aforementioned invention begins to adhere and reabsorb in the tissue so that it can be removed and repositioned quickly, is suitable for manual placement by a practitioner's fingers or using a laparoscopy instrument, and is relatively inexpensive to manufacture.

SUMMARY AND OBJECTS OF THE INVENTION

Accordingly, it is a principal object of the present invention to provide a reinforcing device for effective parietal hernia repair and other reconstructive tissue repairs that can be positioned by a practitioner using an anterior route as well and a laparoscopic route.

It is also an object of the invention to provide a reinforcing device that is suitable for placement in an intra-abdominal or intra-pelvic location using a laparoscopic device that does not require conventional sutures or staples.

It is still another object of the invention to provide a reinforcing device made from a knitted mesh having spiked naps in which at least a portion or all of the knitted mesh and spiked naps on one of the faces of the device are covered with a layer that is dissolvable in a rate-controlling manner.

It is another object of the invention to provide a dissolvable material that may be coated on a monofilament strand of PET and/or a spiked nap of PLA to a pre-determined thickness and that dissolves at a pre-determine rate from the outer contact surface exposed to various solvents.

It is still another object of the invention to include a formulation for a dissolvable matrix having one or more of a biodegradable component, an antibacterial component, an excipient, a therapeutic drug, a plasticizer, and a binder component.

It is another object of the invention to provide a device that is relatively easy for a practitioner to use.

It is still another object of the invention to provide a device that is relatively easy to manufacture.

Briefly described, the above and other objects and advantages of the present invention are accomplished, as embodied and fully described herein, by a reinforcement device for reinforcing tissues having one or more structural deficiencies, such as parietal tissues. The device includes a longitudinally-extending reinforcing layer for treating the structural deficiency, the layer having an upper and a lower face, a flap portion, a slit portion, and a cut-out portion; a plurality of spiked naps distributed across one or both of the faces and the flap portion and projecting therefrom for adhering to the tissue; and a first dissolvable matrix layer covering at least a portion of the reinforcing layer and a portion of the plurality of spiked naps, the matrix layer increasing the time before the spiked naps substantially adhere to the tissue.

The above and other objects and advantages of the present invention are also accomplished, as embodied and fully described herein, by a method for reinforcing tissues having one or more structural deficiencies, the treatment method including the steps of providing a reinforcement device as described above, and holding the reinforcement device at the tissue until at least a portion of the dissolvable matrix layer dissolves, allowing the device to adhere to the tissue.

DETAILED DESCRIPTION OF THE INVENTION

Figure 1:
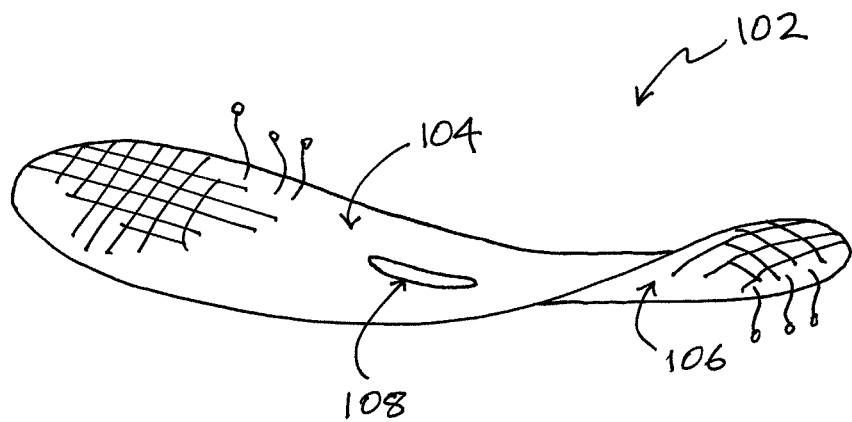
FIG. 1 is a perspective schematic drawing of a reinforcing device according to the prior art.

Several preferred embodiments of the present invention are described for illustrative purposes, it being understood that the invention may be embodied in other forms not specifically shown in the drawings. The figures will be described with respect to the structure and functions that achieve one or more of the objects of the invention and/or receive the benefits derived from the advantages of the invention as set forth above.

Turning first to FIG. 1, shown therein is a perspective schematic drawing of a reinforcing device 102 according to the present invention. The reinforcing device 102 is made substantially in accordance with the device disclosed in U.S. Pat. No. 6,596,002, i.e., a knit which satisfies the requirements of the knits mentioned in the background section of the present description. Thus, the knit may be three-dimensional and open-worked, with two porous faces connected by connecting yarns.

The reinforcing device 102 has an upper face 104 and a lower face 106 and is formed with a cut-out 108 approximately in the center of the reinforcing device 102 as shown. The cut-out 108 has a diameter of about 3 to 7 millimeters.

The knit may be made of a monofilament yarn such as polyester, including PET or similar materials. The knit is flexible, as depicted in FIG. 1, but it could also be made semi-rigid by coating or reacting the yarn with a suitable polymer, plasticizer, or other material.

Figure 2:
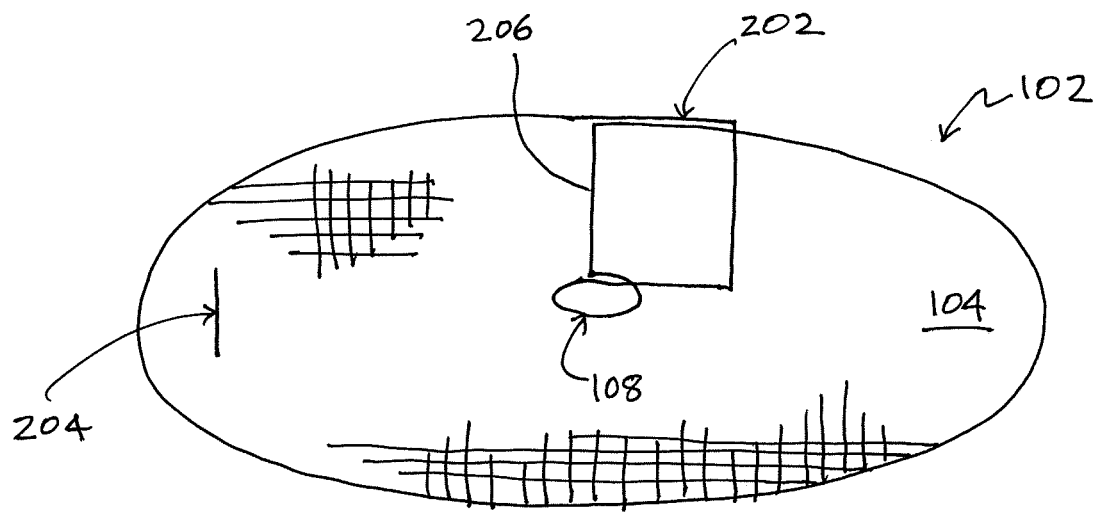
FIG. 2 is a plan view of the reinforcing device of FIG. 1.

Turning now to FIG. 2, shown therein is a plan view of the reinforcing device 102 of the previous figure. As further disclosed in the aforementioned patent, which is incorporated herein by reference, the reinforcing device 102 is generally in the shape of an ellipse. This ellipse includes a large radius of curvature on the upper and lower edges, and a smaller radius of curvature on the left and right edges, respectively. The reinforcing device 102 may be made to other shapes and sizes as needed. It is preferable that the specific edge shape correspond to one or more edges formed by the practitioner in a patient undergoing a procedure to place the reinforcing device 102. This will allow the device to be positioned in the best anatomical position in which it will remain after the procedure.

The reinforcing device 102 includes, about halfway along the length of the upper edge and extending from the cut-out 108 to the upper edge, an end portion 206, which is covered by a flap portion 202. The combination of the flap portion 202 and the end portion 206 forms a slit or opening that is generally perpendicular to the upper edge and parallel to the end portion 206.

Near one edge of the reinforcing device 102 is a cord 204 made from a biocompatible yarn material that is generally stronger than the rest of the material of the reinforcing device 102, and provides a suitable anchor for fixing a conventional suture or staple, if needed. Additional cords 104 could also be added to the reinforcing device 102.

The flap portion 202 has may have the shape shown, i.e., rectilinear polygon, or the shape of a sector of a circular annulus, or some other suitable shape. It may also be a separate piece that is attached to the reinforcing device 102 at one of its linear or arcuate edges. The flap portion 202 extends over a portion of the upper face 104 of the reinforcing device 102 such that when it is joined to the reinforcing device 102 the lower edge is lined up with an edge of the cut-out 108.

As noted in the referenced patent, the flap portion 202 is composed of an open-worked, run-proof knit made, for example, of multifilament synthetic yarns of polyester. In the case where the flap portion 202 is a separate piece, it may be joined or attached to the reinforcing device 102 by a longitudinal stitch or seam that runs parallel to one of the edge of the end portion 206.

The knit used to make the flap portion 202 includes one or more monofilament yarns forming spiked naps projecting from the flap portion 202 or the lower face 106 of the reinforcing device 102 (and/or also projecting from the upper face 104). Depending on the specific medical application, the yarn for these spiked naps may be made of a biocompatible polymer. Suitable polymers include, but are not limited to, polypropylene, or a bioabsorbable material. The bioabsorbable material may include, but is not limited to, polymers of p-dioxanone, polyglycolides, polyorthoesters, polymers of trimethylene carbonate, stereocopolymers of L-lactic acid and D-lactic acid, homopolymers of L-lactic acid, copolymers of lactic acid and a compatible comonomer, such as derivatives of alpha-hydroxy acids.

Figure 3:
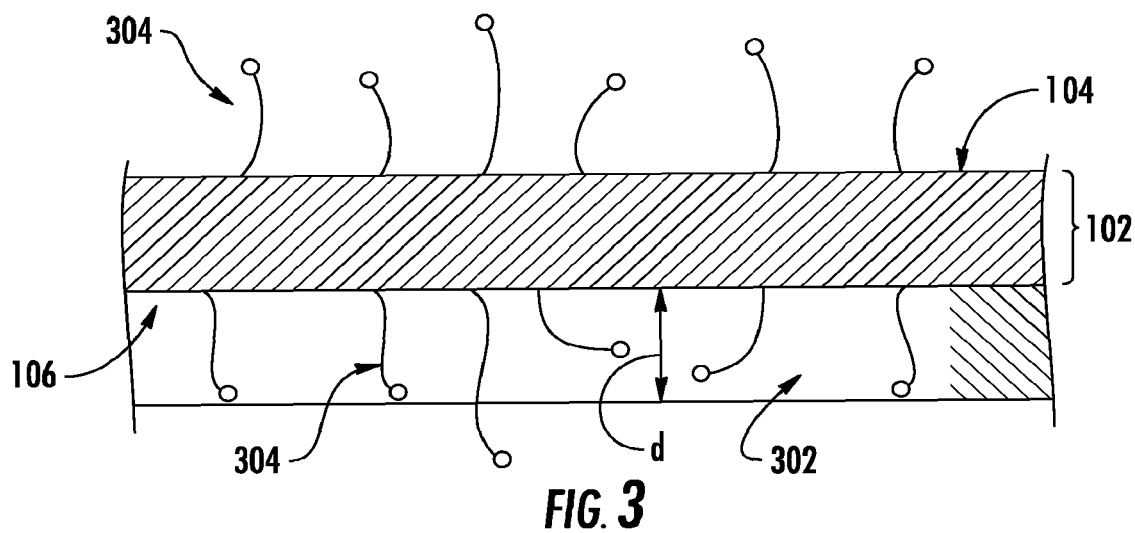
FIG. 3 is a partial cross-sectional elevation view of the reinforcing device according to one aspect of the present invention.

Turning now to FIG. 3, shown therein is a partial cross-sectional elevation view of the reinforcing device 102 according to one aspect of the present invention. Shown therein are several spiked naps 304, similar to those described above in connection with the flap portion 202, projecting from the lower face 106 of the reinforcing device 102. Each of the spiked naps 304 has a length sufficient to penetrate into the knit of the reinforcing device 102 (i.e., between the filaments of the yarns of the knitted structure of the reinforcing device 102). If the knit making up the reinforcing device 102 has a thickness of between 1.5 and 2.2 millimeters, as taught in the referenced patent, the length of the spiked naps 304 measured from their base, projecting from the lower face 106 to the summit of the spike could be between 1 and 2 millimeters, as also taught in the referenced patent. The spiked naps 304 do not have to be linear, and in fact may all have arcuate shaped elongated members terminating with an excess of the PLA material generally in the shape of a flattened ball at the distal end of the spiked naps 304. The terminating end of the spiked naps 304 may also have other shapes, including, but not limited to, a tapered point or J-hook shape.

The density of the spiked naps 304 depends on several factors, but is based on the degree of adhesion required or desired for a particular application. Between 50 and 90 spiked naps 304 per square centimeter of the reinforcing device 102 is disclosed in the referenced patent and is suitable for most parietal reconstruction done from an anterior route. A lower or higher density may be suitable for other types of tissue and procedures.

Covering substantially all of the spiked naps 304 is a dissolvable matrix layer 302 shown in the figure as a thin layer having approximately the same thickness as the reinforcing device 102, i.e., about 1.5 to 2.2 millimeters, though other thicknesses may be used. The dissolvable matrix layer 302 allows the reinforcing device 102 to float as it is being positioned over an area of tissue so that the spiked naps 304 do not immediately adhere to the underlying tissue. As the dissolvable matrix layer 302 dissolves, more of the spiked naps 304 are exposed allowing them to contact the tissue and begin to "adhere" by physical and/or chemical means. The dissolvable matrix layer 302 may extend across the entire lower face 106 (and/or the upper face 104) of the reinforcing device 102, or only a portion of the lower face 106 (or upper face 104).

The dissolvable matrix layer 302 may include one or more of a biodegradable component, an antibacterial component, an excipient, a therapeutic drug, a plasticizer, and a binder component. Other ingredients may also be included.

A variety of polymers are available for the biodegradable component. Suitable polyers include, but are not limited to, methyl cellulose (MC), hydoxy propyl methyl cellulose (HPMC) (commercially: hypromellose), hydroxyl propyl cellulose (HPC), starch and modified starch, Pullulan, Pectin, Gelatin, and carboxy methyl cellulose (CMC). The polymer should account for about 45-percent to 85-percent w/w of the total weight of the dissolvable matrix layer 302. The polymers identified above may be used alone or in combination to obtain the desired rate of mass transfer from the layer to the surrounding. The polymers provide strength and resist damage while handling or during transportation in conventional packaging materials. The strength depends on the type of the polymer(s) and their relative amounts in the dissolvable matrix layer 302. The polymers are non-toxic, non-irritating, and lack leachable impurities. They have good wetting and spreadability properties, making them relatively easy to use in various unit chemical operations such as spray coating, fluidized reactors, pumping, etc. When in use (i.e., in a room temperature aqueous environment), they exhibit gel-like properties since most of the polymers are hydrophilic, and so they exhibit generally low peel strengths making them relatively easy to "float" over a substrate. In solid form, they exhibit good shear and tensile strengths and therefore resist damage from medical instruments. Methyl cellulose in particular can be used as a mild glue which can be washed away with water.

An antibacterial component may optionally be included in the dissolvable matrix layer 302. A suitable non-toxic antibacterial agent includes, but is not limited to, silver ion powder (silver ions in an inert crystalline material). The antibacterial component should account for about 0 to about 5% w/w of the dissolvable matrix layer 302, though higher percentages may be used. The antibacterial component in the dissolvable matrix layer 302 provides a germicidal effect that kills microbial organisms.

A therapeutic drug component may optionally be included in the dissolvable matrix layer 302. The amount of such component may be determined based on the desired dosage, i.e., a mass of drug to a body mass ratio. The therapeutic drug component may be layered deep within the dissolvable matrix layer 302 to reduce loss after the reinforcing device 102 is placed in its final position and is washed (with a saline or water lavage), which can wash away the drug component. It may also be uniformly distributed within the dissolvable matrix layer 302. The drug component can be added to the dissolvable matrix layer 302 as a milled, micronized, nanocrystal, or macro particle, depending upon the release profile desired.

A plasticizer may optionally be included in the dissolvable matrix layer 302. Suitable plasticizers include glycerol, propylene glycol, low molecular weight polyethylene glycols, phthalate derivatives like dimethyl, diethyl and dibutyl phthalate, citrate derivatives such as tributyl, triethyl, acetyl citrate, triacetin and castor oil are some of the commonly used plasticizers used in dissolvable matrices like oral dissolvable strips. The plasticizers account for about 0 to about 20-percent w/w of the dry polymer weight, though a higher percentage may be used. The plasticizers improve the handling properties of the polymer and provide flexibility and reduce the brittleness of the dissolvable matrix layer 302. Other advantages of plasticizers for use in dissolvable layers are discussed in Dixit et al., "Oral Strip Technology: Overview and Future Potential," J. Controlled Release, 139: 94-107 (2009), the content of which is incorporated herein in its entirety.

An optional binder may also be included in the dissolvable matrix layer 302. Suitable non-toxic binders are well known in the controlled release arts. The amount of binder will depend upon the desired rate of dissolution.

Figure 4:
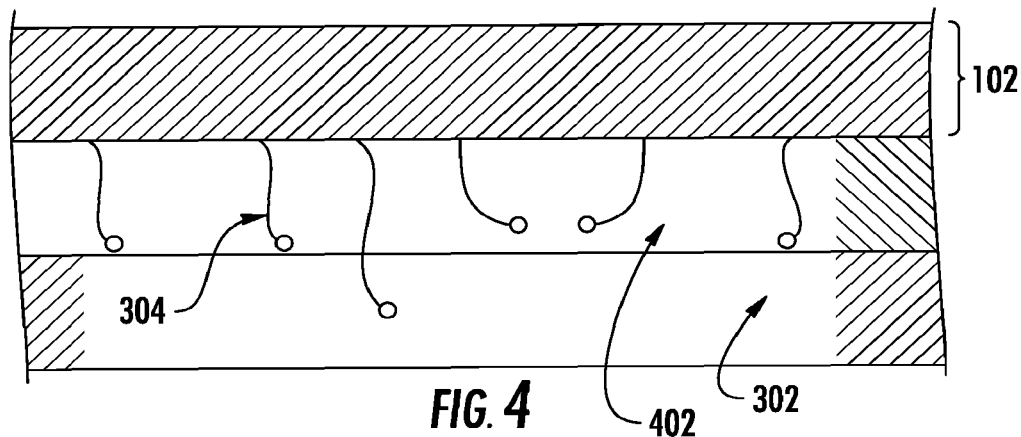
FIG. 4 is a partial cross-sectional elevation view of the reinforcing device according to another aspect of the present invention.

Turning now to FIG. 4, shown therein is a partial cross-sectional elevation view of the reinforcing device 102 according to another aspect of the present invention. In the embodiment shown, a bioadhesive layer 402 may added between the knitted mesh of the reinforcing device 102 and the dissolvable matrix layer 302 such that when the dissolvable matrix layer 302 is removed, the bioadhesive layer is exposed and attaches or adheres to the underlying tissue. The bioadhesive layer 402 may have a variable thickness across the width of the reinforcing device 102, and in another embodiment, only a portion of the knitted mesh is layered with the bioadhesive layer 402. As shown in the figure, it has a thickness of about half or two-thirds of the thickness of the dissolvable matrix layer 302, but the actual layer can be determined based on the specific application in which the reinforcing device 102 is used. The bioadhesive layer 402 is a natural polymeric materials that act as an adhesive, and may be dissolvable or resistant to dissolving (fixed thickness), and, as noted above, is used to supplement the adhesive function of the spiked naps 304 of the reinforcing device 102. Suitable bioadhesives include gelatin, starch, modified starch, certain proteins, carbohydrates, glycoproteins, and mucopolysaccharides, and hydrogels, which can simulate natural tissue.

Figure 5:
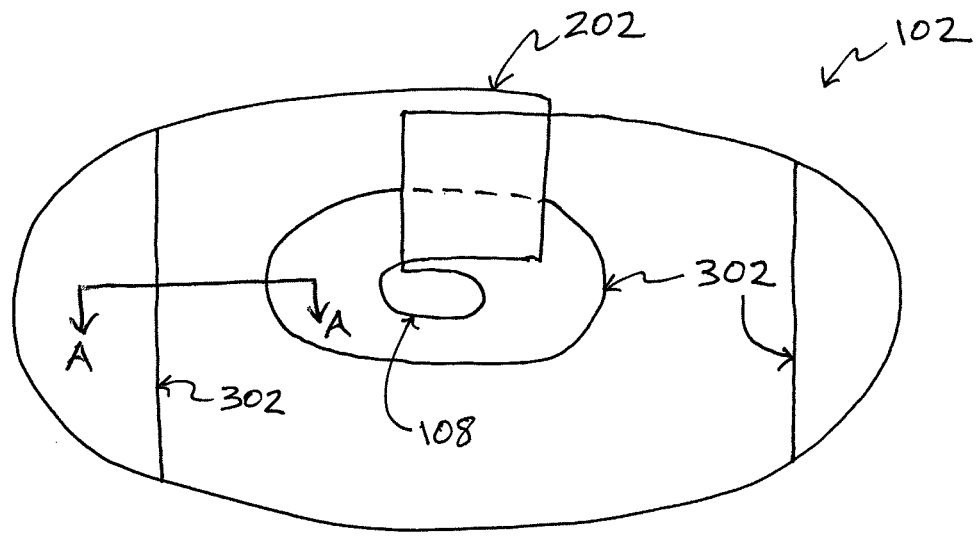
FIG. 5 is a plan view of the reinforcing device of FIG. 1 according to another aspect of the present invention.
Figure 6:
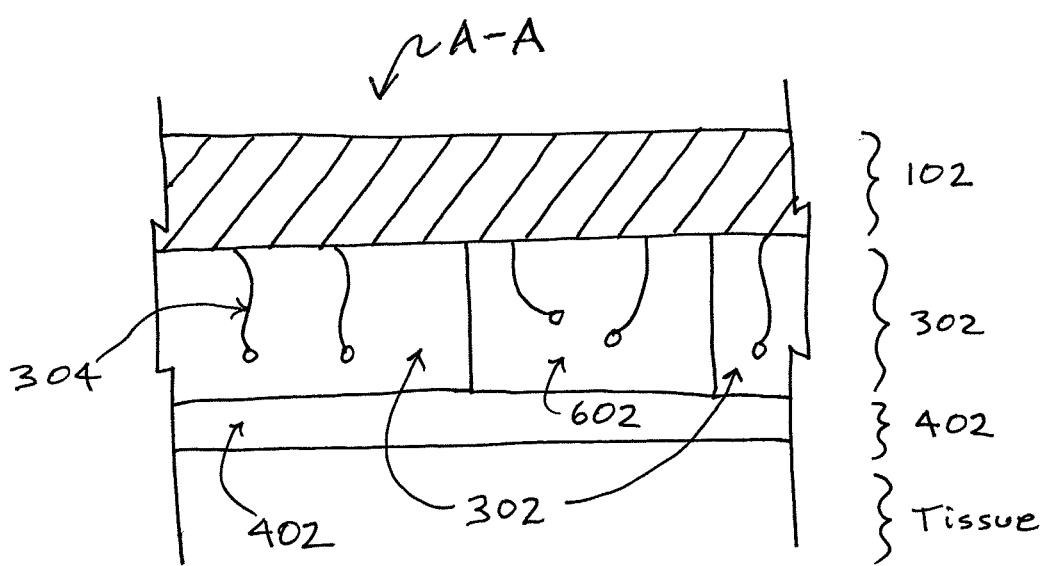
FIG. 6 is a partial cross-sectional view of section A-A of FIG. 5 showing the partial coverage of the reinforcing device with a dissolvable matrix layer and a bioadhesive layer.

One of ordinary skill in the art will appreciate that other layers, or combinations of layers, and their position on the reinforcing device 102, may be used for a particular application. For example, in FIG. 5 the dissolvable matrix layer 302 is shown applied to discrete locations on the reinforcing device 102. Two of the locations are the left and right ends of the device, and the other location is concentric with the cut-out 108. FIG. 6 is a partial cross-sectional view of section A-A (FIG. 5), showing the partial coverage of the reinforcing device 102 with the dissolvable matrix layer 302, and a bioadhesive layer 402, which may be slowly or rapidly dissolvable. The dissolvable matrix layer 302 could be interchanged with the bioadhesive layer 402 in the embodiment shown, such that the dissolvable matrix layer 302 covers the bioadhesive layer 402.

Figure 7:
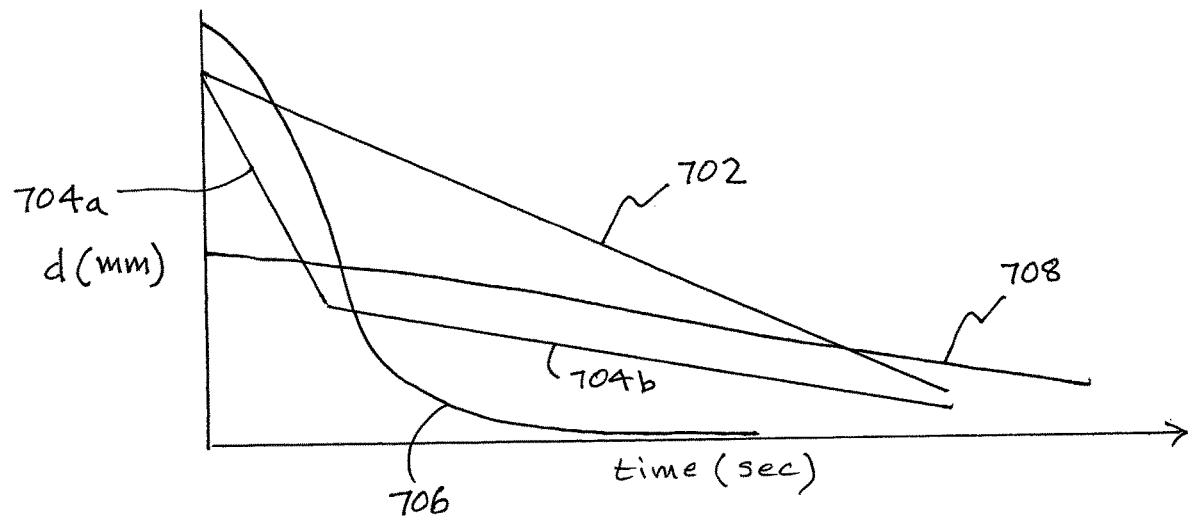
FIG. 7 shows the change in the thickness, d (millimeters), of the dissolvable matrix layer over time.

The dissolvable matrix layer 302 is dissolvable according to a pre-determined, controlled rate, which may be adjusted by using different ingredients or different concentrations of the same ingredients, or by using different solvents or combinations of solvents. Well known mass transfer principles may be used to describe the rate at which the layer dissolves (i.e., convective and diffusive degradation at the solid-liquid interface). FIG. 7 shows the change in the thickness, d (millimeters), of the dissolvable matrix layer 302 over time. Each of the lines shown has a different first- or higher-order dissolution rate over time. Line 702, for example, represents a constant or first-order mass transfer rate at the surface of the dissolvable matrix layer 302 (transfer of solid to a surrounding convective fluid layer at the surface, i.e., the fluid provided by the practitioner as a water lavage when the device is positioned, and/or provided by natural bodily fluids at the site of the reinforcing device 102). Line 704 includes two different rates, 704a and 704b, each with a different rate of mass transfer. Line 706 represents a variable rate of mass transfer, which is rapid initially. Line 708 represents a low rate of mass transfer, whereby the thickness, d, changes slowly over time. Once the dissolvable matrix layer 304 is reduced by about 50-percent, most of the terminal ends of the spiked naps 304 will be exposed.

Figure 8:
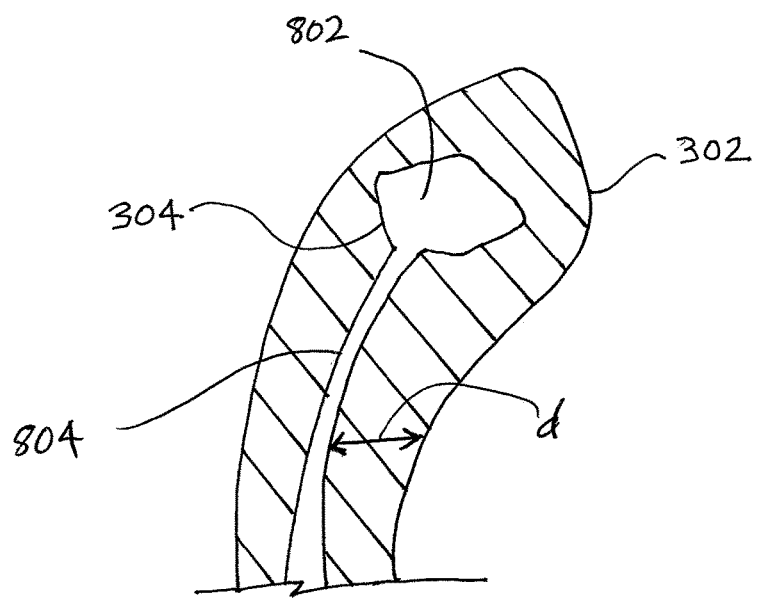
FIG. 8 is a partial cross-sectional view of a single spiked nap according to one aspect of the present invention.

FIG. 8 is a partial cross-sectional view of a single spiked nap 304 having an elongated member 804 and terminating end 802. The spiked nap 304 is shown coated with the dissolvable matrix layer 302 having a thickness, d (millimeters). Since the spiked nap 304 thus coated with the dissolvable matrix layer 302 may extend farther into a bulk fluid (e.g., solvent, such as water), the rate at which the thickness, d, changes over time may be greater than the layer 302 covering the knit of the reinforcing device 102 because of the increased prominence of convective mass transfer compared to diffusive mass transfer closer to the surface of the reinforcing device 102.

In use, the reinforcing device 102 with the dissolvable matrix layer 302 is removed from its packaging material. In the case where a thin film covers the dissolvable matrix layer 302, it is removed by the practitioner prior to use. In a conventional procedure to treat an inguinal hernia, the device is positioned in the anterior inguinal region of a patient and then the area is wetted with a water lavage (or some other solvent is used), which maintains a constant moisture source and helps dissolve the dissolvable matrix layer 302. Dissolution occurs from both sides of the dissolvable matrix layer 302. The anterior surface closest to the knitted mesh of the reinforcing device 102 is dissolved by the solvent as it penetrates the mess. The opposite surface is dissolved by the solvent as it penetrates from the sides of the reinforcing device 102, between the space between the dissolvable matrix layer 302 and the underlying tissue, and by bodily fluids present at the site.

Depending on the thickness of the dissolvable matrix layer 302 or its composition, the spiked naps 304 will begin to be exposed and contact the underlying tissue, at which time they will begin to adhere to the tissue. Without the dissolvable matrix layer 302, the reinforcing device 102 attaches almost immediately, but at least within about 30 seconds. Thus, the time until substantial attachment or adherence is in the range of about 0 to 30 seconds, which is increased with the dissolvable matrix layer 302, such that substantial attachment occurs in a range from about 30 seconds to several minutes, depending, again, on the thickness and composition of the dissolvable matrix layer, and the amount and flow rate of the solvent.

Substantial attachment or adherence is measured in terms of peel strength, i.e., the force, measure in pounds or Newtons per area, required to remove the reinforcing device 102 after its placement on tissue after a pre-determined time period. This parameter is measurable; for example, the peel strength of two objects (one flexible, one rigid) joined together is the average load per unit width of bond line required to part the bonded materials from each other where the angle of separation is 180 degrees and separation rate is 6 in/min (ASTM D-903).

Preferably, the "float" period (i.e., the period before substantial adhesion) according to the present invention is from about 1 to 2 minutes at a peel strength of about 1 to about 3 N/cm, but a much lower peel strength may be desired. That is, when wetted, the dissolvable matrix layer 302 may form a gel that reduces the ability of the spiked naps 304 to adhere and become resorbable. This provides the practitioner sufficient time to assess the initial placement of the reinforcing device 102 and reposition the device as needed before adhesion begins. A faster adhesion would create a higher peel strength and would likely cause trauma to the underlying tissue and damage the reinforcing device 102 if attempts to remove it at that point were to occur.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A reinforcement device for reinforcing tissues having one or more structural deficiencies, comprising:
    a longitudinally extending reinforcing layer for treating the structural deficiency, the layer having a first face and a second face;
    a plurality of naps distributed across at least the first face and projecting therefrom for adhering to tissue;
    a first dissolvable layer including an antimicrobial component covering the plurality of naps, the first dissolvable layer adapted to increase the time before the naps substantially adhere to the tissue; and
    an optional second dissolvable layer covering at least a portion of at least the second face of the reinforcing layer opposite the naps.

2. The reinforcement device of claim 1, wherein the amount of the antimicrobial component is up to about 5% w/w of the first dissolvable layer.

3. The reinforcement device of claim 1, wherein the reinforcement device includes the second dissolvable layer, the second dissolvable layer including a second antimicrobial component.

4. The reinforcement device of claim 3, wherein the amount of the second antimicrobial component is up to about 5% w/w of the second dissolvable layer.

5. The reinforcement device of claim 3, wherein the first dissolvable layer and the second dissolvable layer further comprise one or more of a biodegradable component, an excipient, a therapeutic drug, a plasticizer, or a binder component.

6. The reinforcement device of claim 5, wherein the biodegradable component is a polymer selected from hydroxy propyl methyl cellulose, hydroxyl propyl cellulose, starch and modified starch, pullulan, pectin, gelatin, and carboxy methyl cellulose.

7. The reinforcement device of claim 6, wherein the amount of the polymer is about 45 percent w/w of the total weight of the first dissolvable layer and the second dissolvable layer.

8. The reinforcement device of claim 5, wherein the therapeutic drug is uniformly distributed in the first dissolvable layer and the second dissolvable layer.

9. The reinforcement device of claim 5, wherein the plasticizer is one or more of glycerol, propylene glycol, low molecular weight polyethylene glycols, phthalate derivatives like dimethyl, diethyl and dibutyl phthalate, and citrate derivatives such as tributyl, triethyl, acetyl citrate, triacetin or castor oil.

10. The reinforcement device of claim 1, wherein the reinforcing layer comprises a three-dimensional and open-worked, porous knit.

11. The reinforcement device of claim 10, wherein the knit comprises a monofilament polyester yarn.

12. The reinforcement device of claim 10, wherein the knit has a thickness from about 1.5 millimeters to about 2.2 millimeters.

13. The reinforcement device of claim 1, each nap of the plurality of naps extends from a base to a summit of a spike, and has a length from the base to the summit of from about 1 millimeter to about 2 millimeters.

14. The reinforcement device of claim 1, wherein the plurality of naps have one of an arcuate shape including a flattened ball at a distal end of the plurality of naps, a tapered point, or a J-hook shape.

15. The reinforcement device of claim 1, wherein the reinforcement device comprises a biocompatible polymer.

16. The reinforcement device of claim 15, wherein the biocompatible polymer is one or more of polypropylene, polymers of p-dioxanone, polyglycolides, polyorthoesters, polymers of trimethylene carbonate, stereocopolymers of L-lactic acid and D-lactic acid, homopolymers of L-lactic acid, or copolymers of lactic acid and a compatible comonomer.

17. The reinforcement device of claim 1, further comprising a bioadhesive layer.

18. The reinforcement device of claim 17, wherein the bioadhesive layer comprises one or more of gelatin, starch, modified starch, proteins, carbohydrates, glycoproteins, mucopolysaccharides, or hydrogels.

19. A reinforcement device for reinforcing tissues having one or more structural deficiencies, comprising:
   a longitudinally extending reinforcing layer for treating the structural deficiency, the layer having a first face and a second face;
   a plurality of naps distributed across at least the first face and projecting therefrom for adhering to tissue;
   a first dissolvable layer including a first antimicrobial component covering the plurality of naps, the first dissolvable layer adapted to increase the time before the naps substantially adhere to the tissue; and
   a second dissolvable layer including a second antimicrobial component covering at least a portion of at least the second face of the reinforcing layer opposite the naps.

20. The reinforcement device of claim 19, wherein the amount of the first antimicrobial component is up to about 5% w/w of the first dissolvable layer, and the amount of the second antimicrobial component is up to about 5% w/w of the second dissolvable layer.

* * * * *